United States Patent
Schneider et al.

(10) Patent No.: US 6,749,804 B2
(45) Date of Patent: *Jun. 15, 2004

(54) PROCESS FOR TREATING ANIMAL HABITATS

(75) Inventors: David J. Schneider, Union, KY (US); Jerry K. Bell, Fayetteville, AR (US)

(73) Assignee: H & S Chemical Company, Inc., Covington, KY (US)

( * ) Notice: Subject to any disclaimer, the term of this patent is extended or adjusted under 35 U.S.C. 154(b) by 212 days.

This patent is subject to a terminal disclaimer.

(21) Appl. No.: 09/974,159

(22) Filed: Oct. 9, 2001

(65) Prior Publication Data

US 2002/0076348 A1 Jun. 20, 2002

Related U.S. Application Data

(60) Provisional application No. 60/243,798, filed on Oct. 30, 2000.

(51) Int. Cl.⁷ .............................. A61L 2/00; A61L 2/16
(52) U.S. Cl. ....................... 422/5; 424/76.6; 47/58.1 R; 119/651
(58) Field of Search ............................ 422/5, 16, 78, 422/122; 119/651, 169, 170, 171; 47/58.1 R; 424/76.6

(56) References Cited

U.S. PATENT DOCUMENTS

| | | | | |
|---|---|---|---|---|
| 4,306,516 A | * | 12/1981 | Currey ...................... 119/171 |
| 4,369,199 A | * | 1/1983 | Katzen ...................... 426/641 |
| 5,503,111 A | * | 4/1996 | Hughes ...................... 119/173 |
| 6,196,156 B1 | * | 3/2001 | Denesuk et al. ........... 119/28.5 |
| 2003/0024484 A1 | * | 2/2003 | Schneider ................... 119/651 |

* cited by examiner

Primary Examiner—Robert J. Warden, Sr.

Assistant Examiner—Sean E. Conley

(74) Attorney, Agent, or Firm—Donald R. Bahr

(57) ABSTRACT

This invention deals with a process for treating and sanitizing animal habitats. In addition to sanitizing the habitat the production of ammonia and odor from fecal matter and urine is inhibited or terminated. In the process an animal habitat is cleaned and subsequently treated with trichlormelamine (TCM). The TCM may be applied by spraying the habitat with a solution of TCM, by dusting the habitat with powdered TCM or by treating bedding/litter with TCM. This process produces healthier animals and as such the productivity of a given grow out is increased. The process of this invention is particularly suited to animal habitats which are used to raise batches of hogs, cattle, turkeys and chickens on a continuing basis. The TCM may be further incorporated into water soluble polymeric compositions which permit the TCM to be leached out in a controlled manner. Further the TCM may be incorporated into cellular and noncellular polymeric compositions which may be used as bedding/litter material, and cat litter.

72 Claims, No Drawings

PROCESS FOR TREATING ANIMAL HABITATS

RELATED APPLICATIONS

This Application claims priority of provisional application Ser. No. 60/243,798 filed Oct. 30, 2000.

FIELD OF THE INVENTION

This invention deals with the sanitizing and the improvement of animal habitats wherein the animals are being kept by humans in an agricultural setting. More particularly this invention is concerned with sanitizing and improving animal habitats in order to provide more productive and healthful animals. In accordance with this invention a wide variety of different habitats and situations can be sanitized and improved. The process of this invention comprises the application of trichloromelamine to the habitat environment which contains or will contain bacteria so as to achieve a specific but relatively low residual concentration of trichloromelamine. This treatment with trichloromelamine sanitizes and improves the habitat. Further the invention is concerned with ammonia and odor control.

BACKGROUND OF THE INVENTION

In the past trichloromelamine (hereinafter TCM) has been used extensively to sanitize floors, tabletops, kitchens and kitchen utensils. This sanitization is usually effected by the spraying of a dilute solution of TCM on to surfaces to be treated or objects such as eating utensils, pots and pans etc. These objects may be likewise soaked in solutions of TCM. Further TCM has been used to kill bacteria on foods by the soaking of food in a solution of TCM such as the soaking of fresh vegetables in a solution of TCM. In these environments the concentration of TCM which can be used is carefully controlled by the E.P.A. and the Food and Drug Administration. This control will be discussed in detail herein below.

Soon after man decided to domesticate animals thousands of years ago, man decided that at least in some circumstances it was desirable to keep domesticated animals in a defined space i.e. keeping fowl in a chicken house or hogs in a barn. This keeping of domesticated animals in a defined space resulted in the contamination of the space with fecal matter and urine. This concentration of fecal matter and urine in a confined space results in the space being contaminated with unacceptable levels of bacteria. This bacteria often resulted in the contained animals becoming diseased or less productive.

Further this concentration of fecal matter and urine often resulted in the contamination of the defined space with unhealthy levels of ammonia such that the productivity or health of the contained animals was adversely affected. This fecal matter and urine results in odors which cause troublesome environmental problems.

In modem times the need to provide animals in a habitat with a temperature desirable environment has been recognized. The control of the temperature in animals habitats uses significant energy.

In many cases this energy use is increased when the space in which the animals are confined is vented in order to remove undesirable ammonia. That is as the atmosphere in the habitat is vented new air must be heated or cooled in order to achieve the desired temperature. This process results in increased energy use.

In view of the above points there is a need for a process that will sanitize animal habitats, minimize future ammonia creation, prevent odors and save energy.

In the prior art animal habitats have been treated with aluminum sulfate however these treatments have failed to solve the problems discussed above.

BRIEF DESCRIPTION OF THE INVENTION

The sanitization and control of habitats in which domesticated animals are kept has been a problem which man has addressed since the very beginning of animal domestication. If the habitat in which domesticated animals are kept is not controlled the animals contained can become diseased or their productivity is curtailed.

The containment of animals in a defined space for purposes of domesticating the animals is thousands of years old. This containment of domesticated animals results in unhealthy concentrations of fecal matter and urine. These concentrations can result in bacteria that can cause various maladies and diseases in the contained animals. Further these concentrations of fecal matter and urine can result in the production of ammonia in unhealthy concentrations such that the contained animals can be asphyxiated. In modem times it has become customary to raise large quantities of animals in batches. The animals in these batches are contained in a defined habitat, i.e. a batch of piglets in a hog house or a batch of turkeys in a poultry house. The process of raising a batch of animals to market size is called a grow out.

Prior to starting a new grow out, it is desirable to sanitize the habitat in order to prevent the transfer of diseases from one batch of animals to a new batch of animals in a new grow out cycle.

In the past disinfectants such as lime, bleach, formaldehyde etc. have been used. While the disinfectants have some affect on the bacteria they had no affect on the future creation of ammonia or other odors coming from the fecal matter. Further because of its adverse affects the use of formaldehyde has been banned in many areas.

In accordance with the process of this invention the habitat is treated with trichloromelamine (TCM) prior to starting the grow out process, treatments during the grow out process may likewise be effected. As a result of this treatment the habitat is sanitized, that is the bacteria are killed and the future production of ammonia during the grow out is inhibited or maximized. Because the production of ammonia is inhibited the need to ventilate the habitat is minimize and hence significant energy is saved in that the need to heat or cool new air coming into the habitat is minimized. To put this aspect of the subject invention in other terms by use of the invention, the energy content of a given animal through the grow out is minimized.

Further, the bacteria and ammonia content of the environment is decreased, the animals are healthier in the grow out, and hence the productivity of a batch of animals is enhanced.

The subject invention can be used in connection with all manner of animals i.e. pigs, cows, cattle, ducks, turkeys, chickens, game birds, etc. Because of the low toxicity of TCM to fowl, the process of this invention is particularly suited for use with turkeys, ducks, game birds, and chickens and ducks.

OBJECTS OF THE INVENTION

An object of the invention is an effective way to sanitize an animal habitat.

Another object of this invention is a process whereby the production of ammonia from fecal matter and urine is minimized or eliminated.

Still another object of the invention is a process whereby energy might be saved in the production of domesticated animals.

Another object of the invention is a process whereby the productivity of a grow out of a batch of animals is increased.

A further object of this invention is odor control wherein the odors originate from animal habitats.

DESCRIPTION OF THE PREFERRED EMBODIMENT

As per the above discussion the subject invention deals with a process whereby animal habitats can be readily sanitized. Further in accordance with this invention the creation of ammonia from fecal matter and urine is reduced. The subject invention comprises the treatment of an animal habitat with trichloromelamine (TCM) usually prior to starting a new batch of animals in a grow out. The term grow out relates to the placement of a batch of juvenile animals in a defined habitat and feeding the animals until they reach marketable size whereupon they are slaughtered.

The habitat in which the grow out occurs is used over and over. For example, a poultry house which is used to raise continuing batches of turkeys or chickens.

In order to prevent the transfer of diseases from one batch of animals to another batch, it is imperative that the animal habitat be sanitized after a given batch of animals reaches marketable size and is slaughtered. Traditionally this sanitization has been effected with lime, bleach, formaldehyde, etc.

In accordance with this invention, the habitat is sanitized by treatment with TCM. This treatment may be effected by the dusting of powdered TCM through out the habitat or by treating bedding/litter with TCM, or it may be effected by soaking the total habitat with a solution of TCM. Mixtures and combination of these methods may also be used. In accordance with the above set forth methods, an effective amount of residual TCM is left in the habitat after the sanitizing process is effected.

In a grow out, large quantities of fecal matter and urine are deposited in the habitat. The decomposition of fecal matter and urine in the habitat produces ammonia. This ammonia as a gas becomes a part of the atmosphere of the habitat, i.e. the concentration of ammonia in the air of a poultry house can reach toxic levels. While animals during a grow out develop a tolerance for this ammonia, regardless of this tolerance the presence of ammonia adversely affects the productivity of a given batch of animals. Further the presence of high concentrations of ammonia makes the animals, and in particular fowl, more susceptible to avian diseases. That is animals that are allowed to breathe cleaner air are healthier, and less stressed and hence they produce more meat. For these reasons it is desirable that the ammonia content of the atmosphere of an animal habitat be kept to a minimum or completely eliminated. The raising of poultry in batches is extremely common, if in a poultry house the ammonia level is allowed to reach unacceptable levels the poultry die as a result of airsacculitis or suffocation.

Regardless of the possibility of death, even if the poultry do not die, if they are less stressed they tend to put on more weight and hence the profit for a given grow out is enhanced to both the contract grower and poultry company.

Even small weight increases such as a one ounce increase over a large batch of poultry, 10,000+birds, can result in a significant profit enhancement.

When ammonia is produced it must be vented out of the habitat in order to prevent the adverse effects discussed above. In order to enhance the production of meat in a grow out, it has become common to maintain a desired and pre-selected temperatures in a grow out. This pre-selected temperature will vary from species to species. In order to maintain a given pre-selected temperature energy must be expended. That is the habitat must be heated or cooled in order to maintain the pre-selected temperature depending on the season.

When ammonia is vented out of the habitat incoming air must be heated or cooled in order that the pre-selected temperature for the habitat is maintained.

In accordance with this invention it has been found that when the habitat is treated with TCM, the production of ammonia is minimized. As a result of this decrease in the production of ammonia, less venting is needed, therefore less energy is needed to maintain the habitat at the pre-selected range temperatures. Hence the energy content of a given animal in a grow out is decreased and therefore the cost of raising a given animal is decreased.

While the applicant is not sure of how the TCM decreases ammonia production it is hypothesized that the TCM affects the nitrogen bonding or the nitrogen cycle in such a manner that the production of ammonia is decreased. This question will be discussed in greater detail herein below.

The control of the bacteria in a habitat affects the health of every part of the animal. In this regard if the bacterial content of the litter in which an animal stands is minimized the animals will have healthier feet. For example if the bacterial content of the litter in which chickens stand is minimized the incidence of footpad dermatitis will be decreased. This makes the crop of chicken feet more valuable in any grow out as chicken feet which are effected with dermatitis are not marketable. The poultry feet byproduct is a major component of the Asian poultry business.

Moving up the animal, the body of an unstressed animal tends to put on weight faster than a stressed animal. A diseased animal is naturally stressed, hence a diseased animal tends to put on less weight when compared to a healthy animal.

Continuing up the animal as is mentioned above the subject invention decreases the production of ammonia in an animal habitat, this decrease in ammonia production has very beneficial and healthful effects on the animals in a grow out i.e. as is mentioned above the presence of excess ammonia in a poultry grow out can kill the poultry as a result of airsacculitis among other airborne diseases (aspergillos—Brooden pneumonia and mycoplasmosis). Further the presence of excess ammonia makes poultry more susceptible to infectious bronchitis and laryngotrachetis. The presence of these diseases further depresses the weight gain of a given fowl, or possibly condemns the fowl from further processing.

The subject invention is advantageous in two ways, these being in the control of bacteria and in decreasing the production of ammonia from fecal matter and urine. Bacteria which is controlled by the process of the subject invention include, but is not limited to salmonella, e. Coli etc.

Having a collateral way to enhance the health of contained animals is particularly important at the present time as the use of antibodies on animals in a grow out is being restricted by the FDA. The use of antibodies is being restricted in order to prevent the transfer of resistant strains of bacteria to humans who eat the flesh of the animals that are produced in a grow out.

The fecal matter and urine of the animals contained in the habitat contain substantial quantities of nitrogen bearing compounds. The process of how these nitrogen bearing compounds are converted to ammonia is not fully understood by the applicant. It is felt that the nitrogen bearing compounds may be converted to nitrogen gas $N_2$ which is subsequently converted by nitrogen-fixing bacteria to ammonia.

The applicant speculates that the production of ammonia may be affected by the destruction of the nitrogen-fixing bacteria by the TCM. The destruction of the nitrogen-fixing bacteria by TCM interrupts the nitrogen cycle and thereby prevents the formation of ammonia and hence its release into the atmosphere of the habitat, to the detriment of the animals as may be contained in the habitat.

An initial treatment of a habitat may not be sufficient to impede the production of ammonia from fecal matter and urine throughout the grow out. If this is the case, it is within the scope of this invention to retreat the habitat with TCM at an intermediate point in the grow out. In order to slow down the production of ammonia at an intermediate stage of the grow out. it is preferred that the litter be retreated with TCM as this brings the TCM into direct contact with the problem area namely the fecal matter urine soaked bedding/litter.

The application of TCM in accordance with this invention has indirect insecticide properties in that by lowering the pH, the life cycle of certain insects is interrupted and hence the insect is controlled, i.e. by the application of TCM to a habitat the pH is lowered to less than 5, a point at which the formation and growth of the Darkling beetle will not occur. The Darkling beetle is a major factor in the cross-contamination of avian diseases in poultry houses.

The application of the process of this invention is particularly suited to animal habitats that are used to raise continuing batches of animals for meat production i.e. batches of hogs, chickens and turkeys. In addition the process of this invention can be used in conjunction with other aspects of animal habitats such as sanitizing of hog houses, pens, egg houses, hatcheries, dairy barns, zoo enclosures and it can be formulated into cat litter and litter for other animals.

As is mentioned above the subject invention is useful in egg houses and hatcheries. In these environments this invention is advantageous by decreasing the incidence of bacteria contamination in the production of eggs from laying hens. The control or elimination of bacteria from the beginning of conception produces better egg quality for the commercial egg retail market and for hatching chickens for the poultry/meat market, A sanitized nesting area is key to producing top quality eggs and retail and commercial chicks. The USDA has stated the "egg" hatchery process could be the key to the elimination of e. Coli and salmonella further down the poultry feed chain to the retail market. The application of TCM in the hatchery process is an extremely important step in the reduction or elimination of e.Coli and salmonella. Likewise the production of healthy chicks or poultry for the grow out process is further enhanced by the control or elimination of ammonia in the hatchery From the above discussion it is evident that TCM is an extremely useful biocide and pesticide for use in connection with animal habitats. In this connection cellular and non cellular polymeric materials may be useful carriers for the TCM including cat litter, small animal bedding, and for other animals.

The TCM may be incorporated into various polymers and used as a bedding material. For example the TCM may be incorporated into virgin and recycled polymers such as polyethylene, polypropoylene, polyvinyl chloride, polystyrene etc. Further these mixtures may incorporate a blowing agent and as the mixture leaves an extruder, blowing is effected to form a cellular structure. These cellular structures are then cut or ground into pellets which function as excellent bedding material.

Further the TCM may be formulated into water soluble polymers such as polyvinyl alcohol (PVA), ethyl vinylacetate, and ethylvinyl alcohol and mixtures thereof. These mixtures may then be sprayed in such a manner as to coat the habitat or bedding materials. During the grow out the TCM is leached out of the coating and functions as a biocide and odor control agent as is discussed herein above. These coating compositions may further incorporate agents which control the rate of leaching such that the leaching is conducted at a controlled but predetermined rate. Hence the biocidal and odor control properties are effected at a predetermined rate.

Once a grow out is completed there remains in the habitat a large quantity of fecal matter which is mixed with bedding/litter. This composite material must be disposed of in an environmental friendly manner. The process of this invention is advantageous as it facilitates disposal of the bedding and fecal matter in an environmental friendly manner due to its low bacteria content.

The process of this invention is also advantageous in that when treated in accordance with this invention the habitats are less odorous. The odor control is in addition to the reduction in ammonia as is discussed above. While the applicant is not sure of how this odor control is effected it is felt that the odor control results from the ability of the residual TCM moiety to bond with sulfur, phosphate, and nitrogen bearing molecules. That is when the chlorine is stripped from the TCM molecule an active residual moiety exists. This residual moiety has multiple active sites which can bond with odorous nitrogen and sulfur bearing compounds. The resulting product could produce a slow-release fertilizer in combination with animal waste.

When the habitat is to be sprayed with a solution of TCM in accordance with this invention it is preferred that the solution be formulated from a dry powder having the composition of Table I all parts are by weight.

TABLE I

| | |
|---|---|
| Monosodium Phosphate | 40 |
| Citric Acid | 28.3 |
| Wetting Agent | 13.00 |
| TCM | 18.70 |
| | 100.00 |

The dry powder was dissolved in water at the rate of 0.25 oz. to 3 gal water to give a concentration of about 100 ppm. The solution was sprayed on to the habitat.

EXAMPLES

The present invention is illustrated by the following Examples however, these Examples are not to be construed as limiting the invention. All of the test of Examples 1 to 8 were carried out in 20,000 $Ft^2$ poultry houses.

1. (Prior art) 19,000 chickens were placed in an uncleaned poultry house for a 100 day grow out. The temperatures during the grow out was maintained at 74°±4°. The average moisture content of the bedding was maintained below 14%. The average relative humidity in the house atmosphere ranged from 40 to 84%.

During the grow out the production of ammonia gas was significant. At the end of the grow out period the bird mortality was 50% of the batch. Further 6% of the birds were condemned at the processing house. The average weight for the chickens was 4 pounds.

2. (Prior art) 14,000 poults (turkeys) were placed in an uncleaned poultry house for a 100 day grow out. The temperature during the grow out was maintained at 74±4°. The average moisture content of the bedding was maintained below 14%. The average relative humidity in the house atmosphere ranged from 40 to 74%.

During the grow out the production of ammonia gas was significant. At the end of the grow out period the bird mortality was 8% of the batch. Further 1–3% of the birds were condemned at the processing house. The average weight gain for the turkeys was 22 pounds.

3. (Prior art) A poultry house was prepared by cleaning out the used animal bedding (shaved wood chips) The poultry house was then sprayed with a maximum formulation of formaldehyde. After a 72 hour drying period new shaved wood chips were spread in the poultry house and stocked with 19,000 thousand chickens, temperature of the house was maintained at 74% F±4 degrees F. for the term of the grow out. The terms of the grow out was 45 days, average moisture content in the bedding was maintained below 14%. Average relative humidity in the house atmosphere ranged from 40% to 84%.

During the grow out period, ammonia gas was extremely significant. After two weeks, 200 pounds of alum (aluminum sulfate) was spread evenly on top of the shaved wood chips and dispersed throughout. The average weight gain for the chickens in the grow out was 3.96 pounds. The bird mortality rate was 3.56%. The percentage of birds condemned at the processing facility was 0.15%.

4. (Prior art) a poultry house was prepared by cleaning out the used animal bedding (shaved wood chips). The poultry house was then sprayed with a maximum formulation of formaldehyde. After a 72 hour drying period, new shaved wood chips were spread in the poultry house and stocked with 15,000 thousand poults (turkeys). The temperature of the house was maintained at 74°% F±4 degrees F. for the term of the grow out. The term of the grow out was 100 days, average moisture content in the bedding was maintained below 14%. Average relative humidity in the house atmosphere ranged from 40% to 84%.

During the grow out period, ammonia gas was extremely significant. After two to three weeks, 200 pounds of alum (or aluminum sulfate) was spread evenly on top of the shaved wood chips and dispersed throughout.

The bird mortality rate was 8.1% of the batch, 2.3% of the birds were condemned at the processing facility. The average weight gain for the turkeys in this grow out was 21.8 pounds.

5. A poultry house was prepared by spraying all house surfaces (ceiling, walls, and padding/floor) with a solution of 2 pounds of 18.7% formulated TCM per 300 gallons of water. The concentration of the TCM for the washdown was 200 ppm. 12,000 young poults (turkeys) were then placed in the poultry house for a 100-day grow out. The average temperature of the house was maintained at 78° F.±4 degrees for the term of the grow out. The bedding material used was shaved wood chips. Average moisture content in the bedding was maintained below 14%. Average humidity in the house atmosphere ranged from 40% to 68%. The term of the grow out was 100 days.

During the grow out period ammonia gas was significantly less noticeably when compared to Example 1 and none was noticed at the beginning of the grow out. As the manure and excretions were built up in the shaved wood chips, the ammonia odor increased slightly. In contrast the control of Example 2 house was nauseating to the contract grower and his work crew. No chlorine blow off was detected.

The bird mortality was 2.7%, 1.7% of the birds were condemned at the processing facility. The weight gain for the turkeys was 24.3 pounds.

6. A poultry house was prepared by spraying all house surfaces (ceiling, walls, and padding) after a complete cleanout of previous used wood shavings and manure, with a solution of 2 pounds of 18.7% TCM formulation to 300 gallons of water. The concentration of TCM for the washdown was 200 ppm. 6000 young poults (turkeys) were placed on 3 tons of fresh shaved wood chips in the poultry house. A direct spray-on application of the TCM formulation was sprayed on the new wood shavings and allowed to dry. The solution consisted of 1 pound of formulated TCM to 125 gallons of water or 100 ppm. The average temperature inside the poultry house was maintained at 80 degrees±4 degrees F. for the term of the grow out. Average moisture content in the bedding was maintained below 14%. Average relative humidity in the house atmosphere ranged from 50% to 85%. The term of the grow out was 100 days. The poultry house was retreated via a direct spray-on of the formulated TCM was applied to the bedding material at week 10 of the grow out period for the same batch of turkey poults. The concentration of the TCM in solution was 1 pound of formulated TCM per 125 gallons of water.

During the grow out period, the contract grower reported the TCM treated house had no odor for several weeks. Even at the time of reapplication (direct spray-on) for turkey disease considerations, the ammonia odor was not a problem. In contrast the control house of Example 2 had 5 applications of alum due to the ammonia odor problem by week 10. No chlorine blow-off was detected for the initial washdown or subsequent direct applications. The ammonia odor increased slightly as the added organic manure increased over time. However, the concentration of ammonia never reached the point where it affected the poults.

At the end of the grow out the bird mortality was 0.7%,. 1.4% of the birds were condemned at the poultry processing facility. The weight gain for the birds was 23.9 pounds.

7. A poultry house was prepared by using used bedding material. The used animal bedding (shaved wood chips) and manure had been in use for 18 months without removal. A direct spray on application consisting of a solution of one pound of TCM per 125 gallons of water or 100 ppm was sprayed on top of the used animal bedding. 19,000 young chickens were placed in the poultry house. The average temperature of the house was maintained at 78 degrees F. for the term of the grow out. Average moisture content in the bedding was maintained below 14%. The term of the grow out was 39 days.

During the 39 day grow out period, ammonia gas was not noticeable until the 35th day. A slight odor was noticed at the end of the grow out period. The control poultry house under the same conditions had to be treated 3 separate applications of alum during this period of grow out.

Bird mortality rate was 1.1%. 0.04% of the birds were condemned at the poultry processing facility. The weight gains of the chickens in both poultry houses had an insignificant difference. (Average weight was 4 pounds), the most significant result was the total ammonia gas elimination by applying TCM on 18 month old manure and bedding material for one chicken grow out period.

8. A turkey house was prepared by spraying all surfaces with a solution of TCM. New wood chip bedding was then applied. The concentration was 10 pounds of TCM in 1,600 gallons of water or 190 ppm., 16,000 young poults (turkeys) were then placed in the poultry house for a 100 day grow out.

The purpose of this application was to compare *e.Coli* and salmonella results in a controlled environment as an alternative to formaldehyde, the current sanitizing method used by the poultry industry. At eight weeks of the grow out period after the wash down and the placement of the young poults, a feces sample was acquired from the animal bedding to determine disease levels from both the test poultry house and the control poultry house of Example 1. An independent laboratory tested the two samples.

The test house of this Example had no *e.Coli* or salmonella in the animal bedding material despite the high organic load of the manure. The control poultry house of Example 2 not treated with TCM but on treated, tested positive for Salmonella sp., Group B and *e.Coli* in the animal bedding material. Other avian diseases were positive in the control house and not in the TCM test house. The contract grower also stated a significant reduction of ammonia odor in the TCM test house of this Example in comparison to the control house of Example 2.

9. Test were conducted on hog waste, 3 gallons of hog waste feces, urine and spillage were prepared. These samples had a total bacterial content of 6,100,000 cfu/ml, a Macconkey gram negative rod count of 1,900,000 cfu/ml and an *Escherichia e.Coli*. count of 6,000 cfu/ml. Various solution samples of TCM solutions were prepared and mixed with the 3 gallon samples. The percent kill of these various samples was in accordance with Table III.

TABLE II

PERCENT KILL

| | |
|---|---|
| 4.0 oz. | >99.9998% |
| 3.0 oz. | >99.9998% |
| 2.0 oz. | 99.9996% |
| 1.0 oz. | 99.9998% |
| 0.75 oz. | 99.998% |
| 0.50 oz. | 99.9995% |
| 0.25 oz. | 99.997% |

Further analysis of treated 3 gallon samples are in accordance with Table III

TABLE III

| | Control | TCM 0.25 ounces | TCM 1.75 ounces |
|---|---|---|---|
| Free Chlorine | 0 PPM | 20–50 PPM | 90 PPM |
| Orthophosphates | 350–400 PPM | 200 PPM | 20 PPM |
| Ammonia | 525 PPM | 525 PPM | 430 PPM |
| Sulfate | 40+ PPM | 25 PPM | 0 PPM |
| Nitrate | 30 PPM | 10 PPM | 20 PPM |
| Nitrite | <1 PPM | 0.5 PPM | 0 PPM |

The above description is illustrative only since modifications could be made without departing from the present invention, the scope of which is to be limited only by the following claims:

What is claimed is:

1. A process for reducing the production of ammonia and odors in an animal habitat containing fecal matter and urine comprising the steps of treating said habitat with an effective amount of trichloromelamine wherein the application of trichloromelamine is at a point in time wherein it can affect the production of ammonia and odors from nitrogen and sulfur bearing compounds as may be present in the habitat, and wherein the concentration of trichloromelamine is from about 100 to about 200 ppm.

2. The process of claim 1 wherein the treatment of the habitat with trichloromelamine is prior to the placement of animals in the habitat.

3. The process of claim 1 wherein the treatment of the habitat with trichloromelamine is after placement of the animals in the habitat.

4. The process of claim 1 wherein the treatment of the habitat with trichloromelamine is prior to and after placement of the animals in the habitat.

5. The process of claim 1 wherein the treatment of the habitat is effected by soaking said habitat with a solution of trichloromelamine.

6. The process of claim 2 wherein the treatment of the habitat is effected by soaking said habitat with a solution of trichloromelamine.

7. The process of claim 3 wherein the treatment of the habitat is effected by soaking said habitat with a solution of trichloromelamine.

8. The process of claim 4 wherein the treatment of the habitat is effected by soaking said habitat with a solution of trichloromelamine.

9. The process of claim 5 wherein the concentration of trichloromelamine is from about 25 to about 1000 ppm.

10. The process of claim 6 wherein the concentration of trichloromelamine is from about 50 to about 500 ppm.

11. The process of claim 7 wherein the concentration of trichloromelamine is from about 100 to about 200 ppm.

12. The process of claim 8 wherein the concentration of trichloromelamine is from about 100 to about 200 ppm.

13. The process of claim 1 wherein the treatment of the habitat with trichloromelamine is effected by dusting with powdered trichloromelamine.

14. The process of claim 2 wherein the treatment of the habitat with trichloromelamine is effected by dusting with powdered trichloromelamine.

15. The process of claim 3 wherein the treatment of the habitat with trichloromelamine is effected by dusting with powdered trichloromelamine.

16. The process of claim 4 wherein the treatment of the habitat with trichloromelamine is effected by dusting with powdered trichloromelamine.

17. The process of claim 2 wherein the treatment with trichloromelamine is effected on bedding/litter as is contained in the habitat.

18. The process of claim 3 wherein the treatment with trichloromelamine is effected on bedding/litter as is contained in the habitat.

19. The process of claim 4 wherein the treatment with trichloromelamine is effected on bedding/litter as is contained in the habitat.

20. The process of claim 7 wherein the treatment with trichloromelamine is effected on bedding/litter as is contained in the habitat.

21. The process of claim 8 wherein the treatment with trichloromelamine is effected on bedding/litter as is contained in the habitat.

22. The process of claim 11 wherein the treatment of trichloromelamine is effected on bedding/litter as is contained in the habitat.

23. The process of claim 12 wherein the treatment of trichloromelamine is effected on bedding/litter as is contained in the habitat.

24. The process of claim 15 wherein the treatment of trichloromelamine is effected on bedding/litter as is contained in the habitat.

25. The process of claim 16 wherein the treatment of trichloromelamine is effected on bedding/litter as is contained in the habitat.

26. A process for sanitizing an animal habitat comprising the steps of treating said habitat with an effective amount of trichloromelamine wherein the application of the trichloromelamine is done in such a manner as to bring the trichloromelamine into contact with a bacteria as may be present in the habitat, and wherein the concentration of trichloromelamine is from about 100 to about 200 ppm.

27. The process of claim 26 wherein the treatment of the habitat with trichloromelamine is prior to placement of the animals in the habitat.

28. The process of claim 26 wherein the treatment of the habitat is after placement of the animals in the habitat.

29. The process of claim 26 wherein the treatment of the habitat with trichloromelamine is prior to and after placement of the animals in the habitat.

30. The process of claim 26 wherein the treatment of the habitat is effected by soaking said habitat with a solution of trichloromelamine.

31. The process of claim 27 wherein the treatment of the habitat is effected by soaking said habitat with a solution of trichloromelamine.

32. The process of claim 28 wherein the treatment of the habitat is effected by soaking said habitat with a solution of trichloromelamine.

33. The process of claim 30 wherein the concentration of trichloromelamine is from about 25 to about 1000 ppm.

34. The process of claim 31 wherein the concentration of trichloromelamine is from about 50 to about 500 ppm.

35. The process of claim 32 wherein the concentration of trichloromelamine is from about 100 to about 2000 ppm.

36. The process of claim 26 wherein the treatment of the habitat with trichloromelamine is effected by dusting with powdered trichloromelamine.

37. The process of claim 27 wherein the treatment of the habitat with trichloromelamine is effected by dusting with powdered trichloromelamine.

38. The process of claim 28 wherein the treatment of the habitat with trichloromelamine is effected by dusting with powdered trichloromelamine.

39. The process of claim 29 wherein the treatment of the habitat with trichloromelamine is effected by dusting with powdered trichloromelamine.

40. The process of claim 26 wherein the treatment with trichloromelamine is effected on bedding/litter as is contained in the habitat.

41. The process of claim 27 wherein the treatment with trichloromelamine is effected on bedding/litter as is contained in the habitat.

42. The process of claim 28 wherein the treatment with trichloromelamine is effected on bedding/litter as is contained in the habitat.

43. The process of claim 29 wherein the treatment with trichloromelamine is effected on bedding/litter as is contained in the habitat.

44. The process of claim 30 wherein the treatment with trichloromelamine is effected on bedding/litter as is contained in the habitat.

45. The process of claim 31 wherein the treatment with trichloromelamine is effected on bedding/litter as is contained in the habitat.

46. The process of claim 32 wherein the treatment with trichloromelamine is effected on bedding/litter as is contained in the habitat.

47. The process of claim 33 wherein the treatment with trichloromelamine is effected on bedding/litter as is contained in the habitat.

48. The process of claim 34 wherein the treatment with trichloromelamine is effected on bedding/litter as is contained in the habitat.

49. The process of claim 35 wherein the treatment with trichloromelamine is effected on bedding/litter as is contained in the habitat.

50. The process of claim 36 wherein the treatment with trichloromelamine is effected on bedding/litter as is contained in the habitat.

51. The process of claim 37 wherein the treatment with trichloromelamine is effected on bedding/litter as is contained in the habitat.

52. The process of claim 38 wherein the treatment with trichloromelamine is effected on bedding/litter as is contained in the habitat.

53. The process of claim 19 wherein the bedding/litter is a cellular or non cellular polymeric material.

54. The process of claim 20 wherein the bedding/litter is a cellular or non cellular polymeric material.

55. The process of claim 21 wherein the bedding/litter is a cellular or non cellular polymeric material.

56. The process of claim 22 wherein the bedding/litter is a cellular or non cellular polymeric material.

57. The process of claim 23 wherein the bedding/litter is a cellular or non cellular polymeric material.

58. The process of claim 24 wherein the bedding/litter is a cellular or non cellular polymeric material.

59. The process of claim 25 wherein the bedding/litter is a cellular or non cellular polymeric material.

60. The process of claim 40 wherein the bedding/litter is a cellular or non cellular polymeric material.

61. The process of claim 41 wherein the bedding/litter is a cellular or non cellular polymeric material.

62. The process of claim 42 wherein the bedding/litter is a cellular or non cellular polymeric material.

63. The process of claim 43 wherein the bedding/litter is a cellular or non cellular polymeric material.

64. The process of claim 44 wherein the bedding/litter is a cellular or non cellular polymeric material.

65. The process of claim 45 wherein the bedding/litter is a cellular or non cellular polymeric material.

66. The process of claim 46 wherein the bedding/litter is a cellular or non cellular polymeric material.

67. The process of claim 47 wherein the bedding/litter is a cellular or non cellular polymeric material.

68. The process of claim 48 wherein the bedding/litter is a cellular or non cellular polymeric material.

69. The process of claim 49 wherein the bedding/litter is a cellular or non cellular polymeric material.

70. The process of claim 50 wherein the bedding/litter is a cellular or non cellular polymeric material.

71. The process of claim 51 wherein the bedding/litter is a cellular or non cellular polymeric material.

72. The process of claim 52 wherein the bedding/litter is a cellular or non cellular polymeric material.

* * * * *